(12) United States Patent
Graff et al.

(10) Patent No.: US 8,744,869 B2
(45) Date of Patent: Jun. 3, 2014

(54) INTERACTIVE TEAM PORTAL SYSTEM

(75) Inventors: David S. Graff, Omaha, NE (US); Brian W. Kaiser, Lincoln, NE (US); John M. Wirtz, Lincoln, NE (US)

(73) Assignee: Agile Sports Technologies, Inc., Lincoln, NE (US)

( * ) Notice: Subject to any disclaimer, the term of this patent is extended or adjusted under 35 U.S.C. 154(b) by 1070 days.

(21) Appl. No.: 12/135,736

(22) Filed: Jun. 9, 2008

(65) Prior Publication Data

US 2009/0076843 A1 Mar. 19, 2009

Related U.S. Application Data

(60) Provisional application No. 60/942,603, filed on Jun. 7, 2007.

(51) Int. Cl.
*G06Q 10/00* (2012.01)
*G06F 7/60* (2006.01)
*G06G 7/58* (2006.01)
*G06F 9/45* (2006.01)
*A61B 5/00* (2006.01)
*G06F 19/00* (2011.01)

(52) U.S. Cl.
USPC .................... 705/2; 705/3; 715/723; 386/231

(58) Field of Classification Search
USPC ....................................... 705/2, 3, 4
See application file for complete search history.

(56) References Cited

U.S. PATENT DOCUMENTS

2004/0095378 A1* 5/2004 Vigue et al. ................... 345/723
2007/0201815 A1* 8/2007 Griffin ............................ 386/52

* cited by examiner

*Primary Examiner* — Sean K Hunter
(74) *Attorney, Agent, or Firm* — Tyson B. Benson; Advent, LLP

(57) ABSTRACT

A team communication platform that combines messaging, video, testing, reporting, work flow diagramming, presentations, and performance analysis into a portal system that is made mobile through the use of synchronization services.

20 Claims, 11 Drawing Sheets

INTERACTIVE TEAM PORTAL SYSTEM

CROSS-REFERENCE TO RELATED APPLICATION

This application claims the benefit of and priority to U.S. Provisional Patent Application No. 60/942,603, filed Jun. 7, 2007, entitled INTERACTIVE TEAM PORTAL SYSTEM, which document is hereby incorporated by reference to the extent permitted by law.

BACKGROUND OF THE INVENTION

1. Field of the Invention

This invention relates to team communication, specifically to providing a portal system to facilitate knowledge transfer within a team.

2. Description of Related Art

Teams today are driven by information. Success is often just as much a factor of classroom preparation and mental training as it is physical training. Even the most gifted workers will not find success in the workplace unless they have a solid understanding of their tasks to complete and the resources they have at their disposal.

Team leaders face the challenge of mentally training their team members as well as physically training them. There exists a wealth of information and leaders must filter and deliver that which is relevant to their team in a way that is comprehensive yet still maintains the team members' attention.

Teams today are continually looking to new technologies to enhance this content delivery process. There exist a variety of solutions that attempt to address this need, but even the best information technology infrastructures have a number of significant shortcomings that keep them from truly empowering teams.

Within the sports team realm, current attempts are plagued by a failure to place the technology directly in the team member's hands, instead focusing on team leaders. Furthermore, current attempts fail to provide a comprehensive solution. Video viewing and commenting, work flow (or, in the sports team realm, playbook) viewing and editing, messaging, and reporting are currently separated into disparate systems that do not adequately interact. Additionally, current attempts fail to take a holistic approach, combining the many facets of a team leader or team member's experience into a single portal. Current systems are further plagued by a lack of mobility. Existing stationary systems for knowledge transfer discourage team member use by requiring the individual to be at a specific location using a stationary workstation. Also, current attempts often result in the duplication of work. Due to teams having a limited number of stationary workstations at their disposal, leaders are required to maintain both a library of videos, work flow diagrams, and reports on a server and a printed version of all of these for team member use. Finally, current attempts suffer from a lack of personalization, failing to allow full content customization. Team leaders cannot send content directly to the team member(s) that needs it, and cannot monitor a team member's use of the system and progress through content or exams. The majority of these attempts exclusively address sports applications.

An example of a previous attempt to address these unresolved needs involves video editing and tagging solutions for teams (see, for example, XOS TECHNOLOGIES. However, this attempted system does not currently provide a system that puts video and playbook software in the team member's hands. A further elaboration on this attempted system incorporates freehand notations into play diagrams from Tablet PCs (see, for example, SAGIO SOFTWARE. However, this attempted system does not incorporate video into its solution and is focused primarily on analysis software from a statistical standpoint.

Another example of an attempted system provides a video game simulator in which teams use video game controllers and laptop computers to simulate football games that incorporate their team's plays against mock defenses (see, for example, GRIDIRON TECHNOLOGIES. Teams can enter a variety of plays and potential scenarios to be run with custom-built players whose sizes, strengths and speeds can be set to match those of the team's own players and opponents. However, this type of system focuses solely on simulating in-game scenarios in a realistic game environment and not incorporating interactive videos, reports and work flow diagrams.

Another example of an attempted system provides team members with access to videos from home by allowing server access for the viewing and downloading of video clips on any computer with Internet access (see, for example, COACH-COMM or DARTFISH. Providing access to these items over the Internet, however, presents a potential security issue in that unauthorized users can more easily gain access to this information when it does not require proprietary software to view. Furthermore, this type of system fails to present a holistic solution that incorporates a virtual playbook and interactive reports with video, and the videos presented cannot be commented on using digital ink and text annotations, and voice recordings.

Another example of an attempted system uses Tablet PC technology for video viewing and annotation (see, for example, LRSSPORTS), but offers this system only as a solution for coaches, not for players, and focuses its application on immediate corrections as opposed to distributing corrections post fact.

Although most video editing and tagging platforms allow for teams to burn DVDs or prepare VHS tapes for their players to review and some have allowed for viewing of video over the Internet or on portable devices such as Video IPODs, there still remains a large gap wherein these videos cannot be customized and annotated for each team member, and cannot be transferred over a network to a portable device for team member review. DVDs or VHS tapes are cumbersome and require the physical transfer of the media source. Similarly, portable devices, such as IPODs, require a direct physical connection to the media source to download videos and, with limited screen dimensions, fail to provide players with a resolution that enables them to read coaches' notes or diagrams that are placed directly on the video. Solutions that rely on remote storage of content and only allow videos to be viewed over the Internet do not provide portability for plane or road trips, are limited by the speed at which video can be streamed over the web, require constant network connectivity to function, and present a security concern.

BRIEF SUMMARY OF THE INVENTION

This invention presents a solution that addresses these limitations and directly confronts the core challenges facing teams.

The invention revolutionizes team communications by taking what are currently unstructured, informal lines of communication and formalizing them in a way that maximizes potential knowledge transfer. With the invention, any time that a team leader thinks up a new work flow variation, notices a valuable process correction on video or learns something that is pertinent for a report, that team leader can log in to the system from any location with an Internet connection and broadcast at least that information out directly to their team or any subset of team members that they desire. Similarly, any time a team member has a question or comment for a team leader or another team member, that individual can directly link a work flow diagram or video into his or her message and receive feedback immediately.

The invention takes a team's existing video editing infrastructure, work flow diagramming, reporting processes, and tests and shifts these activities to an interactive, easy-to-use, digital platform. This provides the team with a more powerful and secure means of communication, training, and team management.

Accordingly, several advantages of the invention are:

(a) Interactive Video. The invention provides team leaders and team members the opportunity to utilize interactive videos in which leaders can deliver personalized comments integrated into a video to any other team member or leader. Comments can include sketches directly on the video, typed notes, handwritten notes, and voice recordings at multiple points throughout a video clip. Videos can be integrated into any other area of the invention, including the work flow diagrams, reports, tests, and messages. Team leaders and team members can review any clip in their personalized video library at any time with full annotations automatically displayed during playback.

(b) Virtual Work Flow Diagrams. The invention provides teams with virtual work flow diagrams in which team leaders and team members can navigate through the most updated diagrams of work flows and strategies that outline team member interaction and how processes are completed. Specific to a sports team application, work flow diagrams can include plays. A work flow diagram can have videos, voice recordings, written comments, and report information directly linked to it. Work flow diagrams can be updated and immediately transferred to every team member's computer when synced. Furthermore, each work flow diagram can be stored with multiple variations based on various scenarios, and team members can quickly "self-test" themselves on any work flow diagram by wiping instruction sets off the diagram, recreating them, and receiving immediate feedback from the system on the accuracy of the recreation.

(c) Knowledge Check. Team leaders can create a customized test for any team member or group of team members, with test questions that require an individual to react to scenarios through videos, confirm understanding of work flows through work flow diagrams, and/or answer traditional multiple choice and fill-in-the-blank questions. Team members receive immediate feedback on the accuracy of their answers and team leaders receive continuous updates on a player's performance on tests.

(d) Interactive Reports. Team leaders and team members can drill down to various levels of information, allowing for more detailed data than paper reports can provide. Reports can include information about a team's performance and goals, and competitors' performance. Specific to a sports team application, reports can include scouting reports. The addition of video to these reports adds an interactive element that increases and enhances the information uptake and retention of the reports for team members. Report information can also be incorporated in other relevant areas of the system, with past reports maintained in the system so they can be easily accessed at a later date.

(e) Team Leader's Reports. Team leaders can track a team member's usage of the system, including time spent actively reviewing each work diagram and studying video, as well as performance on tests. They can review the most up-to-date team reports with the ability to review historical reports on all team members.

The present invention revolutionizes team communications by taking what are currently unstructured, informal lines of communication and formalizing them in a way that maximizes the potential knowledge transfer. The system shifts a team's existing video editing infrastructure, work flow diagramming, reporting processes, presentations, and tests to an interactive, easy-to-use, digital platform that provides the team with a powerful and secure means of communication, training, and team management.

DETAILED DESCRIPTION OF THE INVENTION

Figure 1:
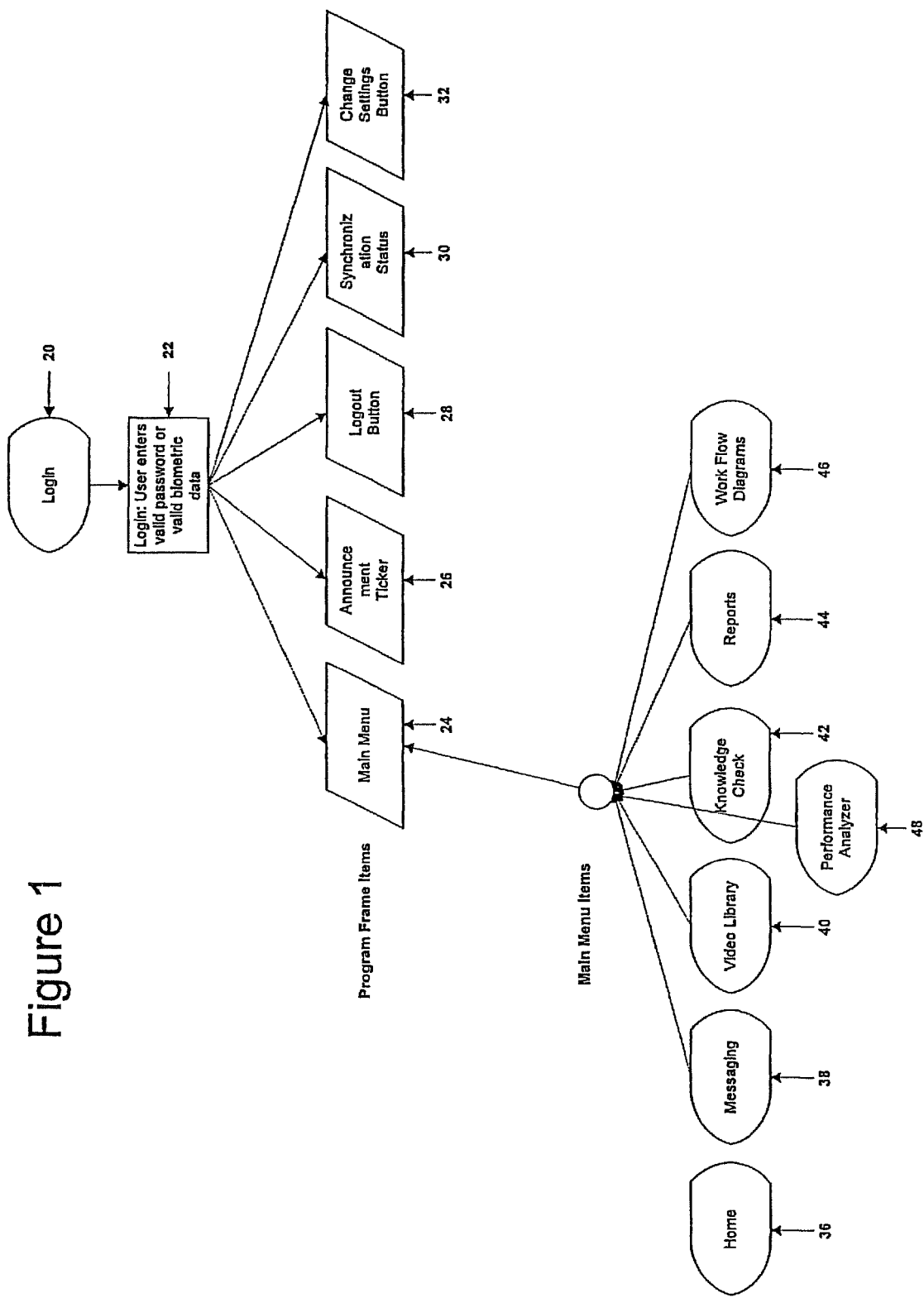
FIG. 1 shows an embodiment of overall flows of the present invention, including a login process, program frame items, and main menu items.

FIGS. 1-7 illustrate an embodiment of a system of the present invention. Note in FIG. 1: System Flow, a user shall enter a system through a login screen 20. The user shall then login by entering a unique user identification string, a valid password or valid biometric data 22. Once inside said system, the user shall then be presented with a plurality of program frame items. Included among these said program frame items are a main menu 24, an announcement ticker 26, a logout button 28, a synchronization status message 30, and a change settings button 32.

Main menu 24 items shall include, but are not limited to, links to a home item 36, a messaging item 38, a video library item 40, a knowledge check item 42, a reports item 44, a work flow diagrams item 46, and a performance analyzer item 48.

Announcement ticker 26 shall feature the ability to include rich site summary, or RSS, feeds as well as the ability for a team leader to create a RSS announcement feed that is displayed for all team members.

Logout button 28 shall serve to completely log the user out of said system, close said system and destroy all cached information so that stored information cannot be accessed until the user logs back into said system.

Synchronization status 30 shall serve to keep the user updated on synchronization status and the last time that said system accessed the server and updated data.

Figure 2:
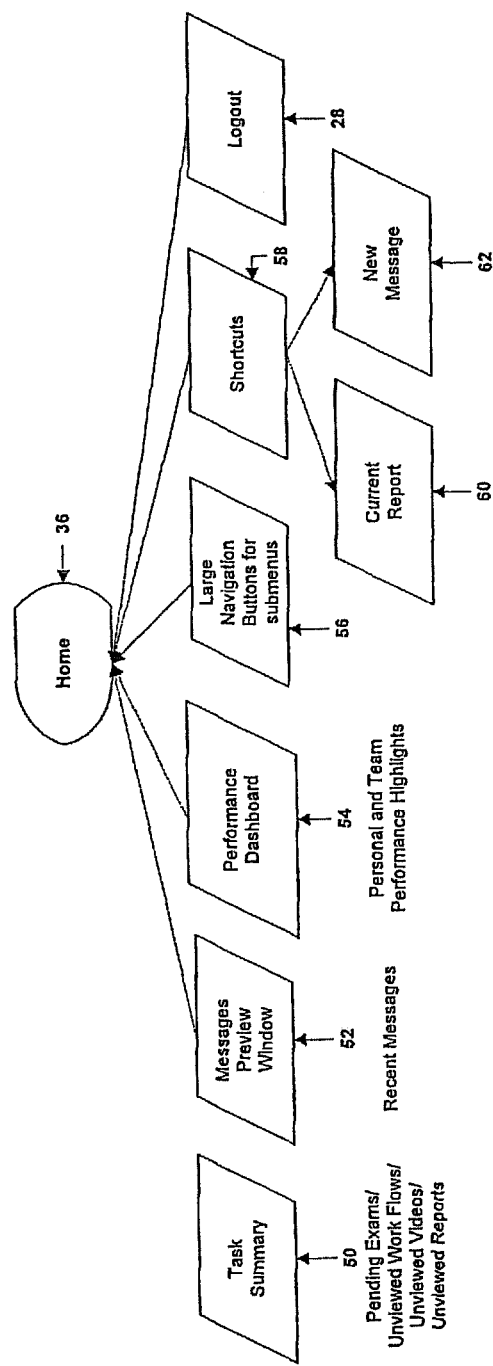
FIG. 2 shows an embodiment of home page flow.

Change settings button 32 shall enable the user to change user-specific settings within said system. FIG. 2: Home Page Flow details the specifics of home item 36. Home item 36 shall serve as the user's home page, displaying a task summary 50, a messages preview window 52, a performance dashboard 54, large navigation buttons for sub menus 56, shortcuts 58, and a logout button 28.

Task summary 50 shall include a listing of all of the user's tasks remaining, including pending exams, unviewed work flows, unviewed videos, upcoming events, and unviewed reports.

Messages preview window 52 shall display a subset of all recently received messages, with unread message distinguished from read messages.

Performance dashboard 54 shall display personal and team performance highlights as well as a means for tracking and displaying both personal and team goals, and for tracking the personal goals of a fellow team member if enabled.

Large navigation buttons for submenus 56 will be included to make it simple to traverse said system and allow the user to easily navigate to his or her destination.

Shortcuts 58 shall include, but not be limited to, links to a current report 60 and a link that takes the user to the create new message screen 62.

As above, logout button 28 will serve to completely log the user out of said system, close said system and destroy all cached information so that no information stored can be accessed in said system after logout has occurred.

Figure 3:
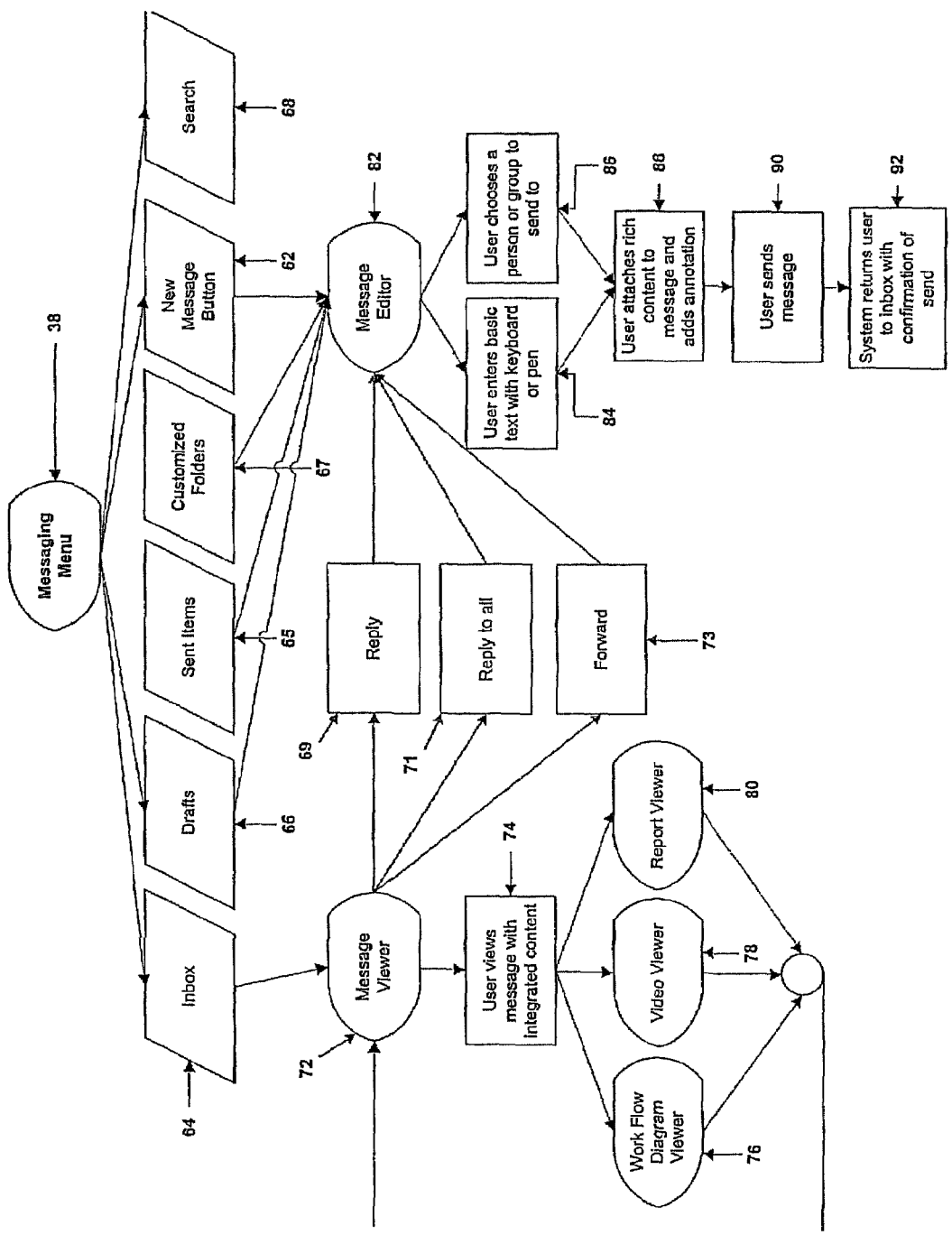
FIG. 3 shows an embodiment of messaging flow.

FIG. 3: Messaging Flow details the specifics of messaging frame 38. Messaging frame 38 shall serve as the user's messaging interface, including links to an inbox 64, sent items 65, an outbox 66, customized folders 67, a create a new message button 62, a reply button 63, a reply to all button 65, a forward button 67, and a search interface 68. Messages can include drawing or inking from an input device such as a mouse or a stylus, or text, as well as integrated content 74.

Inbox 64 shall display all messages a user has received but not deleted or archived, with unread messages distinguished from read messages. Inbox 64 shall be displayed by default whenever the user clicks on the messaging frame 38 for the first time after said system has been entered. Once the user clicks on a message 70, a message viewer 72 is displayed. Message viewer 72 allows the user to view the message with text or drawings and integrated content 74, with embedded links to a work flow diagram viewer 76, a video viewer 78, and a report viewer 80.

Sent items 65 shall display all messages that have been composed. The user will be notified when the sent item is synchronized to the server.

Customized folders 67 shall be additional folders for message organization that are defined by the user or the system administrator.

New message button 62 shall allow the user to create a new message 82. Within create a new message 82, the user can enter basic text or drawn comments with a keyboard or a stylus and choose which users or groups should receive the message 86. The user can also attach rich content to the message and add annotations 88. Once the user sends the message 90, the system returns the user to the inbox 64 with conformation of the send 92.

Search 68 shall allow the user to search messages for key words or a plurality of words appearing in the message subject or message body.

Reply 69 shall allow the user to reply to the sender of the message. The contents of the original message shall be included in the reply along with a text or drawn additions made by the replier. Additional recipients can also be added to the reply by the replier.

Reply to all 71 shall allow the user to reply to the sender of the message along with all others who received the original message. The contents of the original message shall be included in the reply along with a text or drawn additions made by the replier. Additional recipients can also be added to the reply by the replier.

Figure 4:
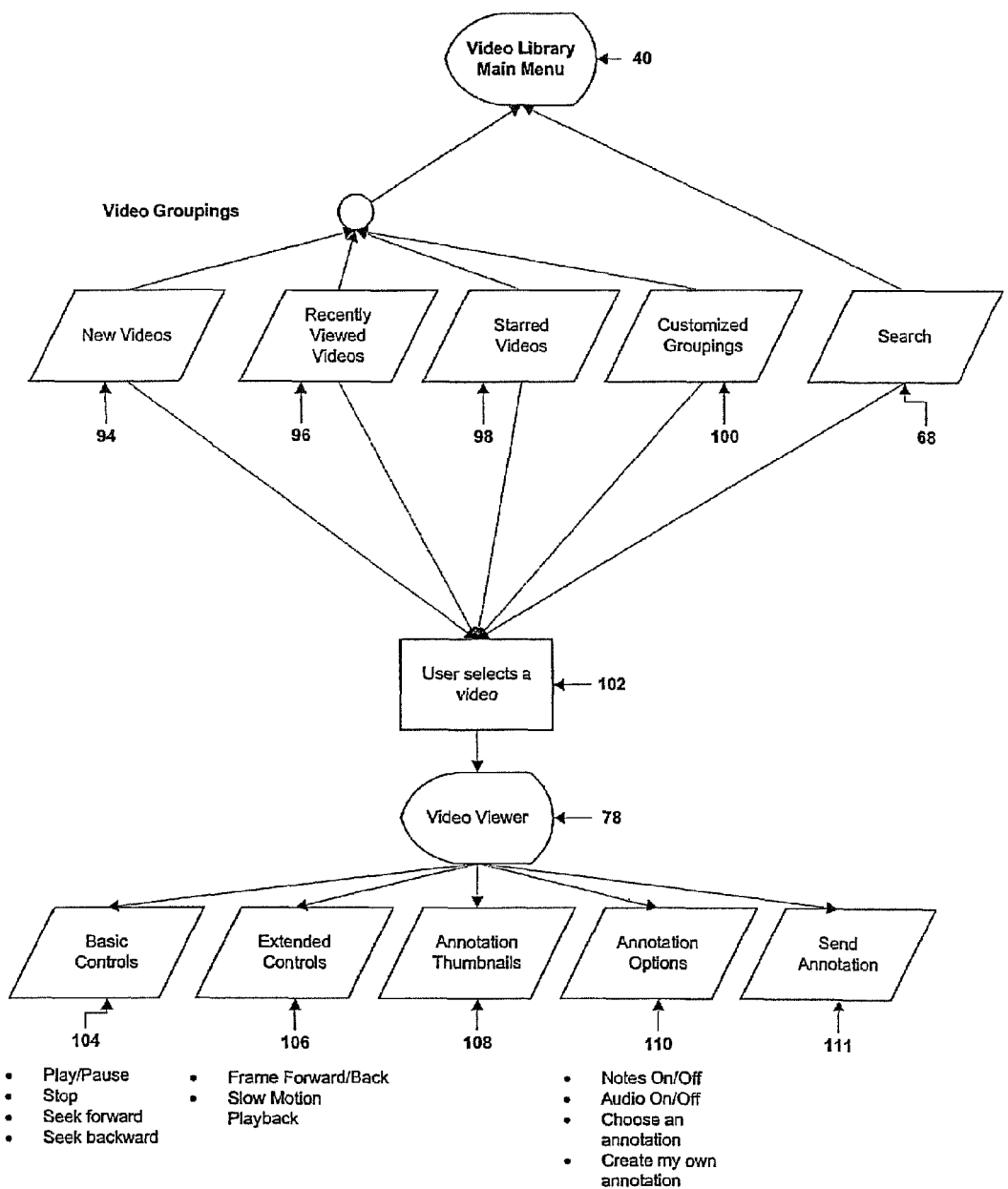
FIG. 4 shows an embodiment of video library flow.

FIG. 4: Video Library Flow details the specifics of video library frame 40. Video library item 40 shall serve as the user's video selection interface, displaying video groupings for new videos 94, recently viewed videos 96, starred videos 98, and customized groupings 100, as well as feature a search functionality 68.

New videos 94 shall include all videos that have been sent to the user that have not yet been viewed. The videos shall be able to be sorted within this interface by any of the data associated with the video, such as date, time, or categorization data.

Recently viewed videos 96 shall include all videos viewed within a specified time period.

Starred videos 98 shall include all of those videos that have been marked by the user marking the star, or other indicator, next to, or in conjunction with, the video.

Customized groupings 100 shall be additional groupings for video storage that are defined by the user or the system administrator.

Search 68 shall allow the user to search the video library for key words or a plurality of words appearing in the video title and allow the user to sort the video groupings and clips by any of the data associated with the video, such as date, time, or categorization data.

Once the user selects a video 102 from any of these groupings or searches, the user is directed to the video viewer 78 that includes basic controls 104, extended controls 106, annotation thumbnails 108, annotation options 110, and send annotation 111.

Basic controls 104 include play, pause, stop, seek forward and seek backward.

Annotation thumbnails 108 are small screen captures of drawn, text, or audio annotations that have been linked to a frame of video.

Annotation options 110 include the ability to turn notes on or off, turn audio on or off, choose an annotation for the video to jump directly to, and create an annotation. Annotations are automatically saved by the system when created for viewing and editing by the creator, but are not distributed.

Send annotation 111 enables the creator of an annotation to send the video clip and any set of annotations to any user or group available in the system.

Figure 5:
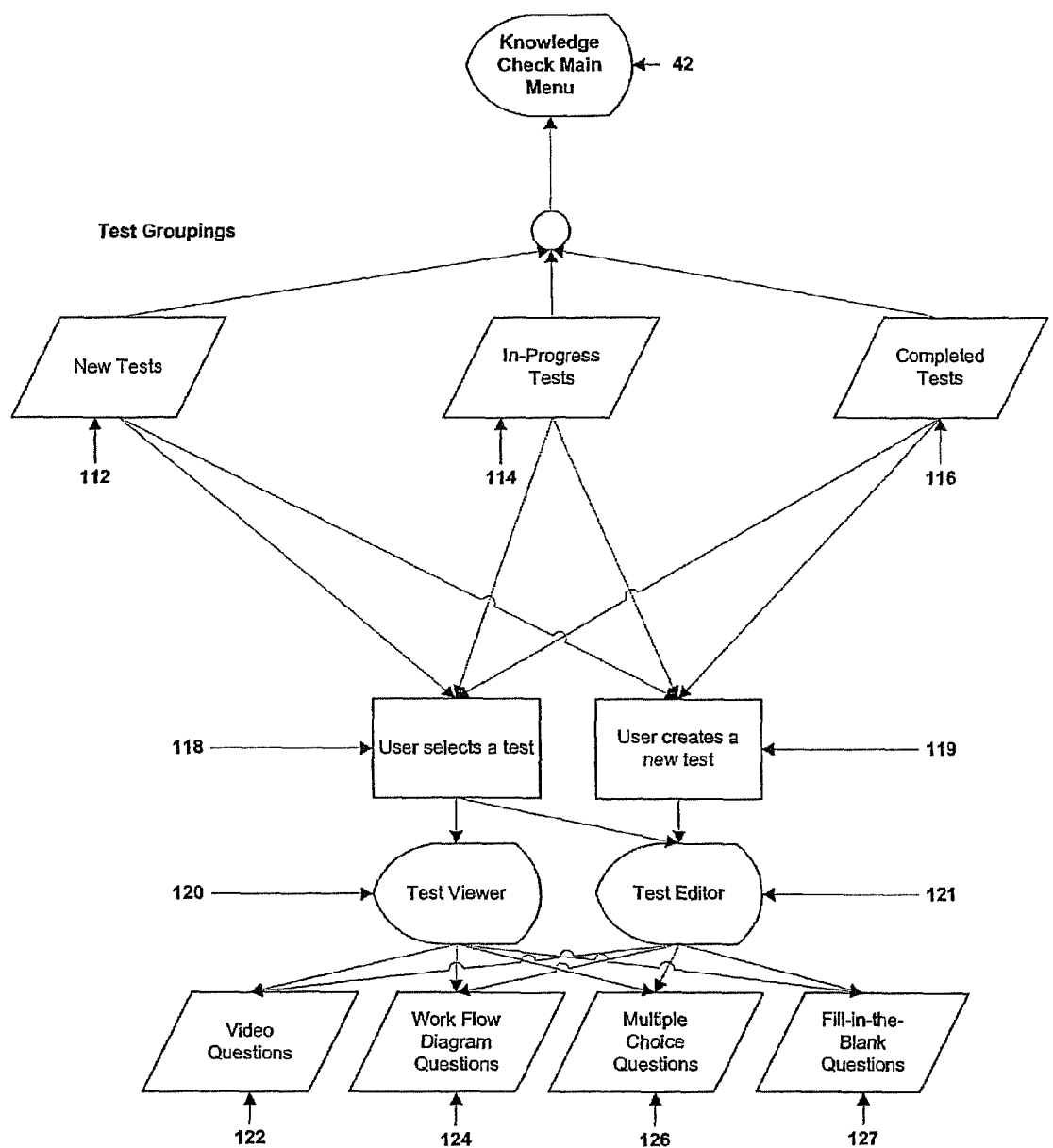
FIG. 5 shows an embodiment of knowledge check flow.

FIG. 5: Knowledge Check Flow details the specifics of knowledge check item 42. Knowledge check item 42 shall serve as the user's testing interface, displaying test groupings for new tests 112, in-progress tests 114, and completed tests 116.

New tests 112 shall include all tests that have not yet been started.

In-progress tests 114 shall include all tests that have been started, but not yet completed. Some tests will be set so that they must be completed in one sitting. In this case, the test will never be listed as an in-progress test.

Completed tests 116 shall include all tests that have been started and completed.

Once a user selects a test 118 from one of these lists, he or she shall, dependent upon his or her privileges, he or she shall be able to choose to be directed to a test viewer 120 that displays the selected test, including video questions 122, work flow diagram questions 124, multiple choice questions 126, and fill-in-the-blank questions 127, or a test editor 121, wherein he or she shall be able to modify the test, including the video questions 122, work flow diagram questions 124, multiple choice questions 126, and fill-in-the-blank questions 127.

Dependent upon privileges, a user shall be able to choose to create a new test 121 which directs him or her to a test editor 121, wherein he or she shall be able to modify the test, including the video questions 122, work flow diagram questions 124, multiple choice questions 126, and fill-in-the-blank questions 127.

Video questions 122 shall feature videos with related questions that could require the user to select an object on the video (or the proximity of an object) or answer multiple choice questions 126 or fill-in-the-blank questions 127 based on the video content.

Work flow diagram questions 124 shall feature work flow diagrams with related questions that could require the user to recreate the work flow by removing the flows and having a the user redraw them or require the user to answer multiple choice questions 126 or fill-in-the-blank questions 127 based on the work flow diagram content.

Multiple choice questions 126 shall require the user to select an answer or a plurality of answers from a selection set. Multiple choice questions 126 shall be able to be incorporated into video questions 122 or work flow diagram questions 124.

Fill-in-the-blank questions 127 shall require the user to type or draw an answer or a plurality of answers to a question. Fill-in-the-blank questions 127 shall be able to be incorporated into video questions 122 or work flow diagram questions 124.

Figure 6:
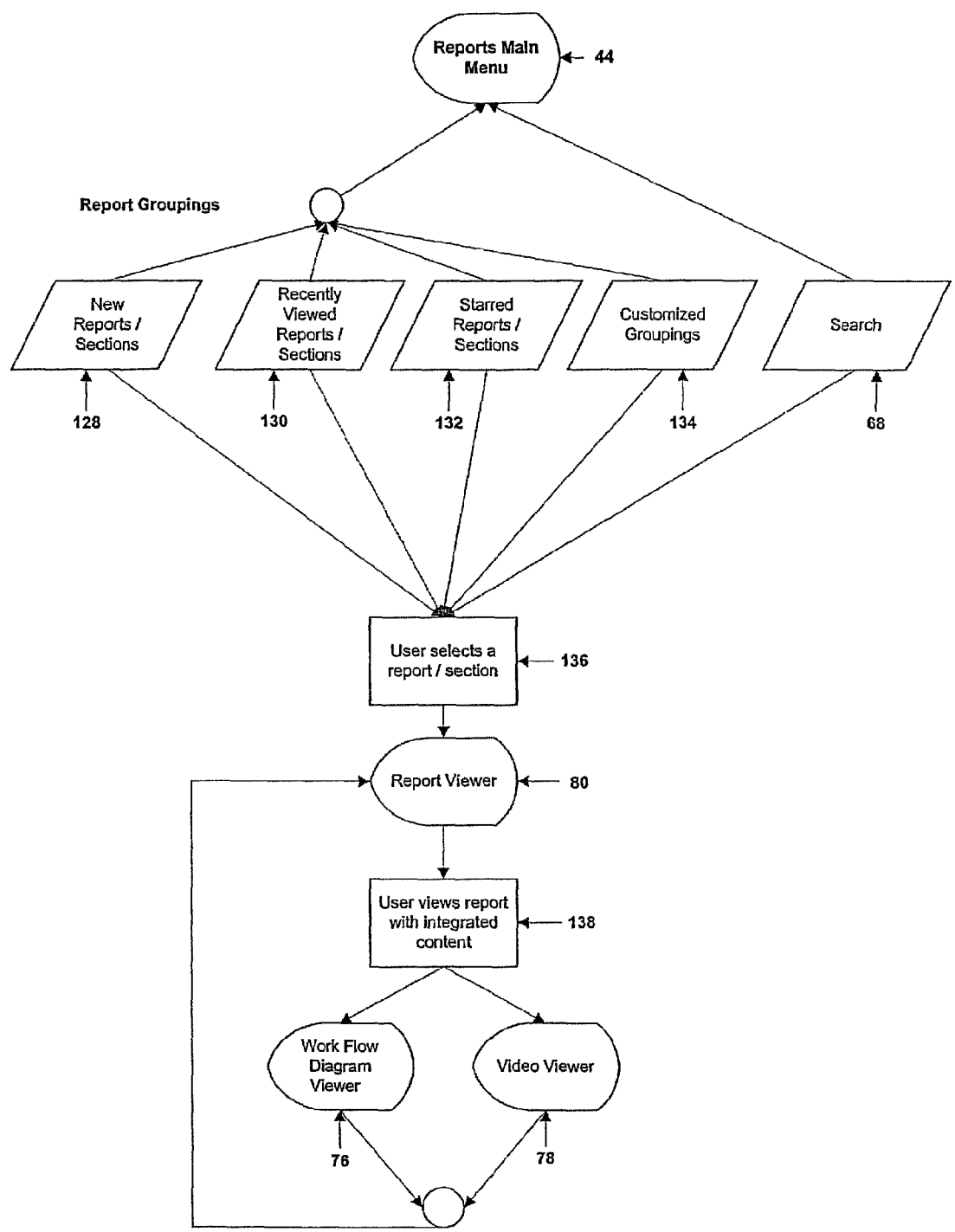
FIG. 6 shows an embodiment of report flow.

FIG. 6: Reports Flow details the specifics of reports item 44. Reports item 44 shall serve as the user's reports interface, displaying report groupings for new reports/sections 128, recently viewed reports/sections 130, starred reports/sections 132, and customized groupings 134, as well as feature search functionality 68.

New reports/sections 128 shall include all reports and sections of reports that have been sent to the user for review but have not yet been viewed. The reports shall be able to be sorted within this interface by any of the included data associated with the report or section, such as date, time, or categorization data.

Recently viewed reports/sections 130 shall include all reports/sections viewed within a specified time period.

Starred reports/sections 132 shall include all of those reports/sections that have been marked by the user marking the star next to the report/section.

Customized groupings 134 shall be additional groupings for report/section storage that are defined by the user or the system administrator.

Search 68 shall allow the user to search the reports for key words or a plurality of words appearing in the report content or the report title and allow the user to sort the reports by any of the included data associated with the report or section, such as date, time, or categorization data.

Once the user selects a report/section 136, report viewer 80 is displayed. Report viewer 80 allows the user to view the report with integrated content 138, including embedded links to the work flow diagram viewer 76, and video viewer 78.

Figure 7:
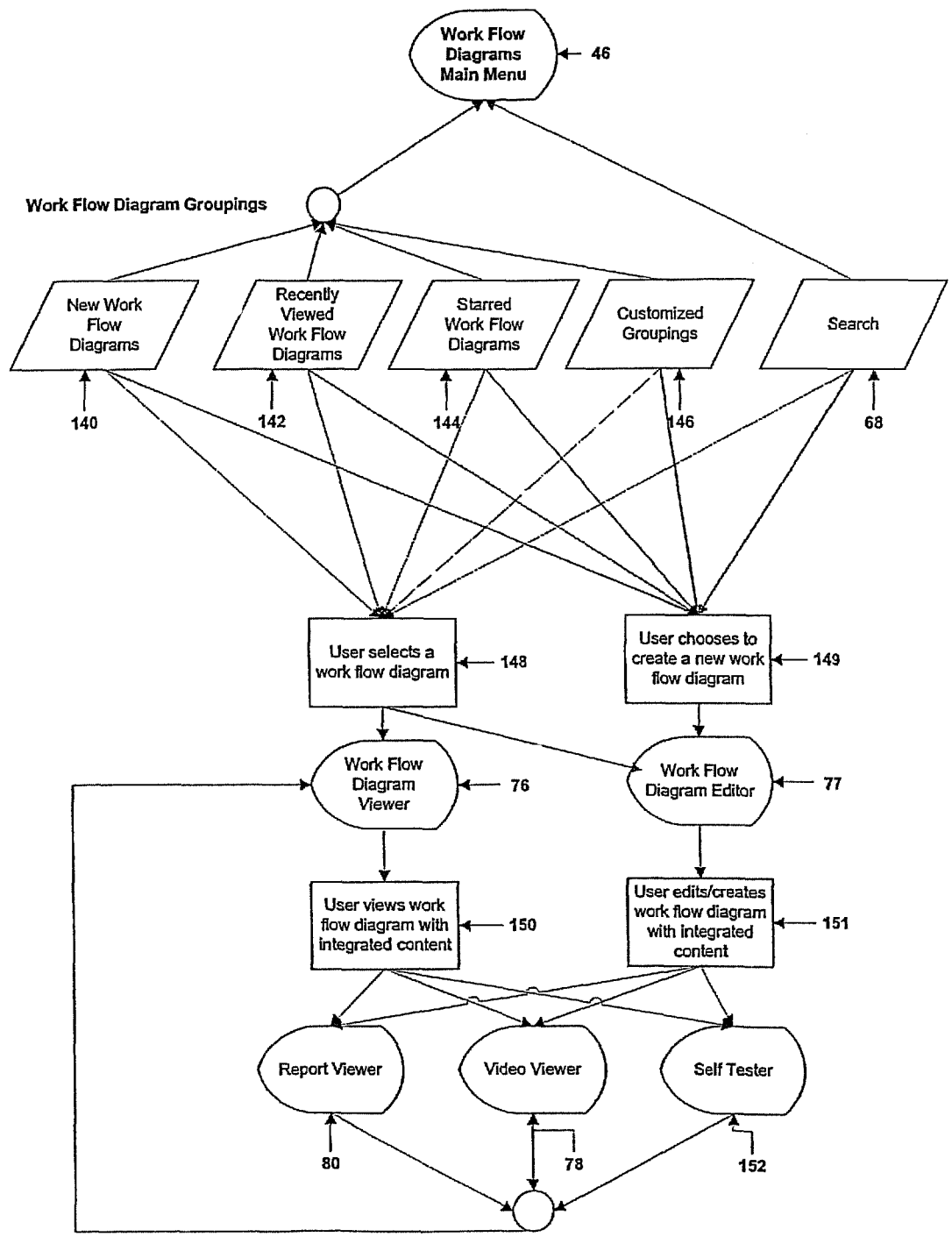
FIG. 7 shows an embodiment of work flow diagrams flow.

FIG. 7: Work Flow Diagrams Flow details the specifics of work flow diagrams item 46. Work flow diagrams item 46 shall serve as the user's work flow diagrams interface, displaying work flow diagram groupings for new work flow diagrams 140, recently viewed work flow diagrams 142, starred work flow diagrams 144, and customized groupings 146, as well as feature a search functionality 68.

New work flow diagrams 140 shall include all work flow diagrams that have been sent to the user for review but have not yet been viewed. The work flow diagrams shall be able to be sorted within this interface by any of the included data associated with the diagram, such as date, time, or categorization data.

Recently viewed work flow diagrams 142 shall include all work flow diagrams viewed within a specified time period.

Starred work flow diagrams 144 shall include all of those work flow diagrams that have been marked by the user marking the star next to the work flow diagrams.

Customized groupings 146 shall be additional groupings for work flow diagrams storage that are defined by the user or the system administrator.

Search 68 shall allow the user to search the work flow diagrams for key words or a plurality of words appearing in the work flow diagram title and allow the user to sort the work flow diagrams by any of the data associated with the diagram, such as date, time, or categorization data.

Once the user selects a work flow diagram 136, dependent upon his or her privileges, he or she may choose to be directed to either a work flow diagram viewer 76 or a work flow diagram editor 77.

Work flow diagram viewer 76 allows the user to view the work flow diagram with integrated content 150, with embedded links to report viewer 80, video viewer 78, and a self tester 152, wherein the user can quickly "self-test" themselves on any work flow diagram by wiping instruction sets off the diagram, recreating them, and receiving immediate feedback from the system on the accuracy of the recreation.

Work flow diagram editor 77 allows the user to edit or create a work flow diagram with integrated content 151, with embedded links to report viewer 80, video viewer 78, and a self tester 152, wherein the user can quickly "self-test" themselves on any work flow diagram by wiping instruction sets off the diagram, recreating them, and receiving immediate feedback from the system on the accuracy of the recreation.

Dependent upon privileges, a user shall be able to choose to create a new work flow diagram 149 which directs him or her to a work flow diagram editor 77, wherein he or she shall be able to edit or create a work flow diagram with integrated content 151, with embedded links to report viewer 80, video viewer 78, and a self tester 152, wherein the user can quickly "self-test" themselves on any work flow diagram by wiping instruction sets off the diagram, recreating them, and receiving immediate feedback from the system on the accuracy of the recreation.

Figure 8A:
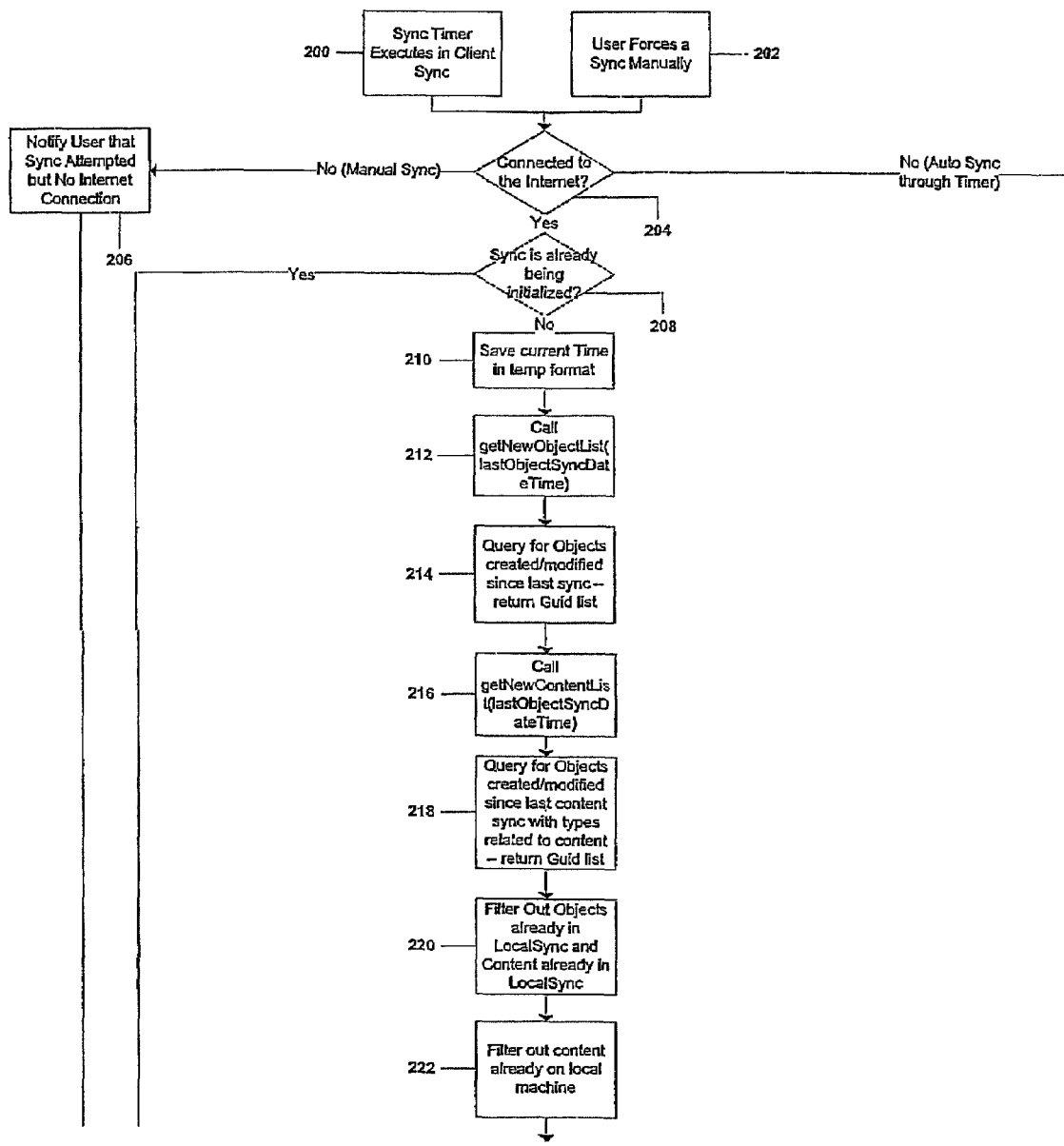
FIG. 8 shows an embodiment of synchronization flow.
Figure 8B:
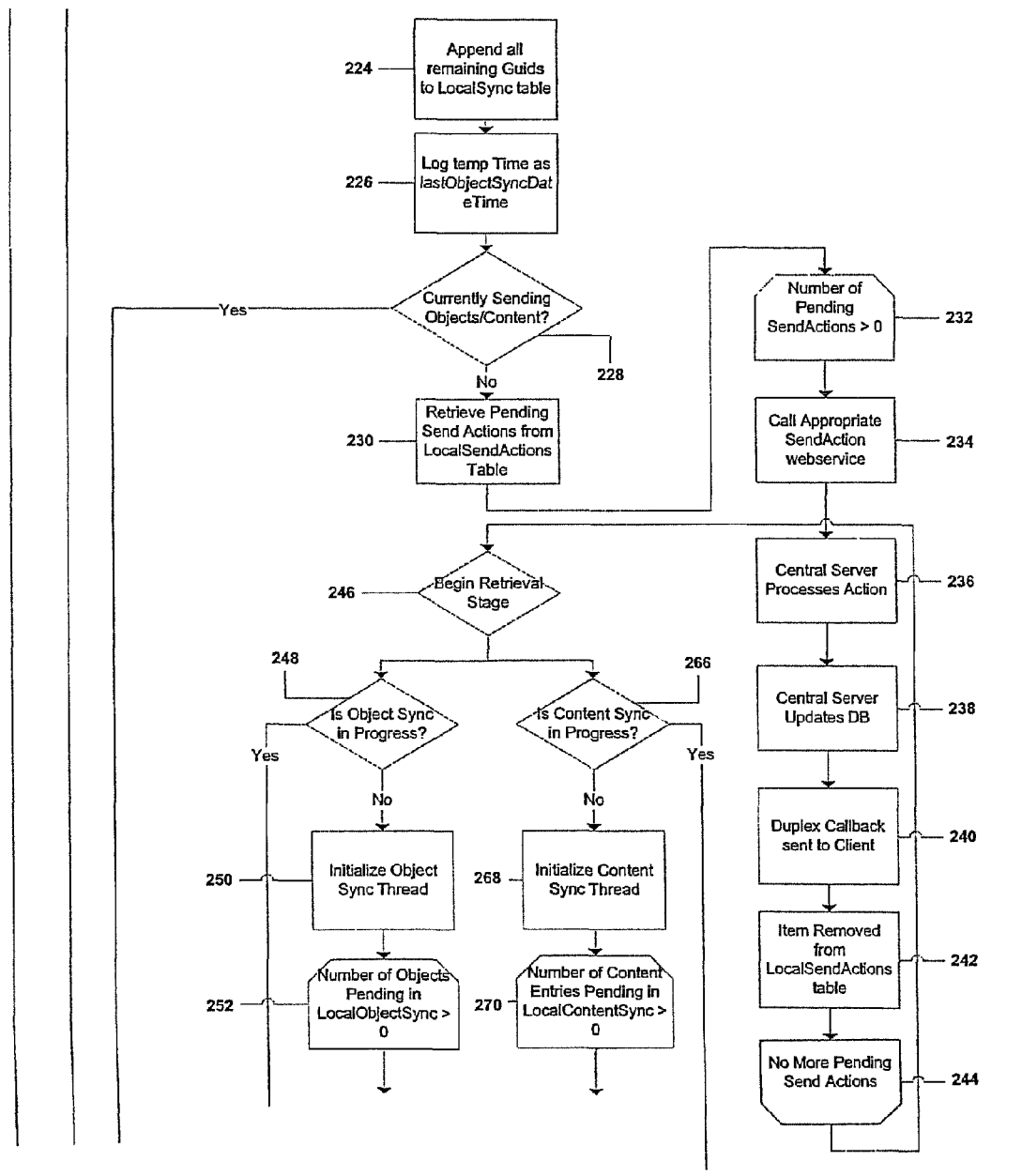
Figure 8C:
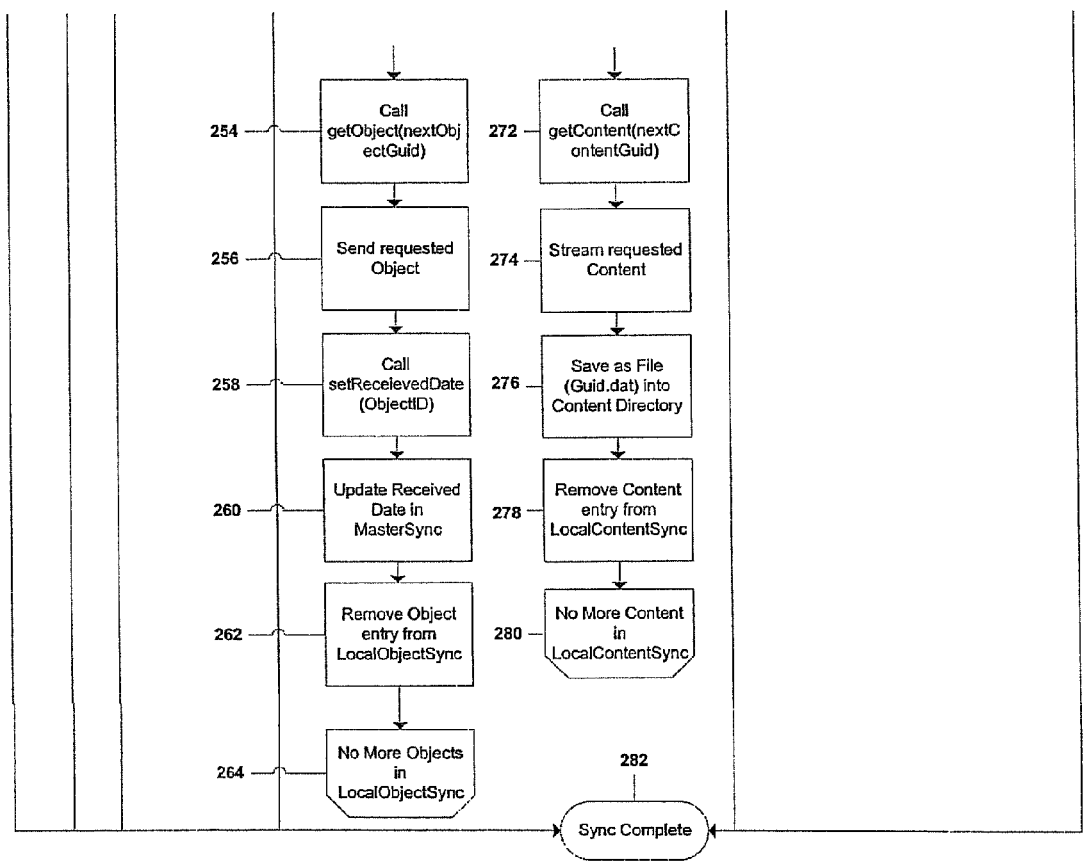
Figure 9:
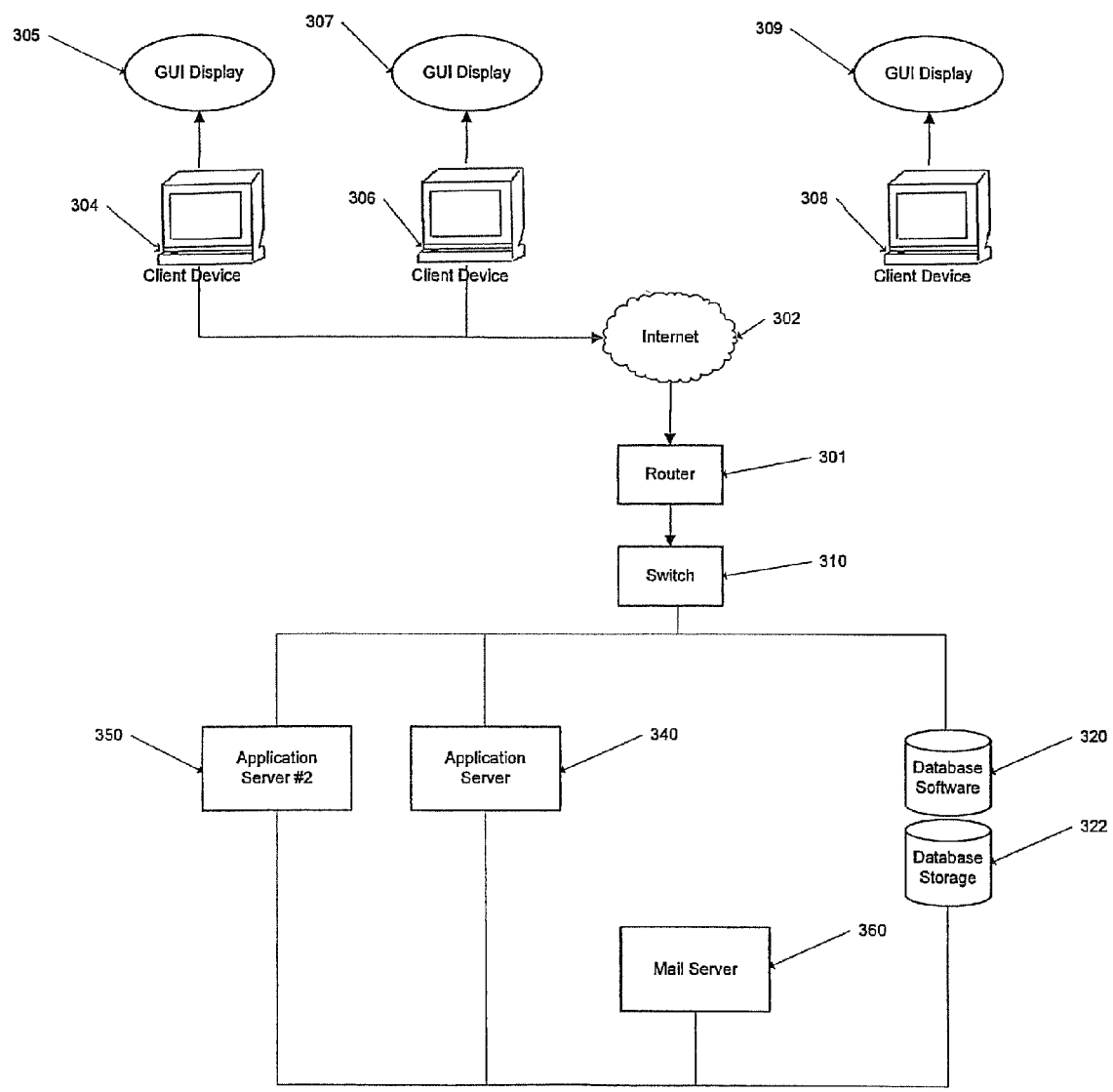
FIG. 9 shows an embodiment of the overall network architecture.

Operation—FIGS. 8-9

As illustrated in FIG. 8: Synchronization Flow, client synchronization is initiated by either a sync timer that executes in client sync 200 or by the user forcing a sync manually 202. Regardless of how the synchronization is initiated, the system first checks to see if the computer is connected to the Internet 204.

If the computer is not connected to the Internet and the synchronization was requested manually 202, the user is notified that the sync was attempted but that no Internet connection was available 206 before the sync is considered complete 282. If the computer is not connected to the Internet and the synchronization was requested automatically through the sync timer 200, no notification is displayed and the sync is considered complete 282.

If the computer is connected to the Internet, the system then checks to see if a sync is already being initialized 208. If one is, then the sync is considered complete 282. If not, the system continues the synchronization process by first saving the current time in a temporary format 210 for later use. The system then calls the getNewObjectList(lastObjectSyncDateTime) function 212 in order to query for objects created or modified since the last sync and returns a Guid list 214. The system then calls the getNewContentList(lastObjectSyncDateTime) function 216 in order to query for objects that were created or modified since the last object sync with types related to content and returns Guid list 218.

The system then performs clean-up functions on the lists, filtering out objects and content already in LocalSync 220, and filtering out content already on the local machine 222 and appending all remaining Guids to the LocalSync table 224 and logging the temporary time recorded earlier as the IastObjectSyncDateTime 226.

The system then checks to see if it is currently sending objects or content 228. If it is, then the sync is considered complete 282. If it is not currently sending objects or content 228, the system will retrieve pending send actions from the LocalSendActions table 230.

If the number of pending SendActions is greater than zero (0) 232, the system calls appropriate SendAction web service 234, which results in central server processes action 236. The central server then updates the database 238 and a duplex callback is sent to the client 240 resulting in the item being removed from the LocalSendAction table 242. This process is repeated until there are no more pending send actions 244.

Once all pending send actions have been handled, the system begins the retrieval stage 246, which begins by checking to see if an object sync is in progress 248 or a content sync is in progress 266.

If an object sync is currently in progress 248, then the object sync process is considered complete 282. If it is not, then the system initializes an object sync thread 250. If the number of objects pending in LocalObjectSync is greater than zero (0) 252, the system calls the getObject(nextObjectGuid) function 254 which results in the server sending the requested object 256 and the system calling the setReceievedDate(ObjectID) function (if this is the first time that the client has received this object) 258. The system then updates the received date in MasterSync 260 and removes the object entry from LocalObjectSync 262. This process is repeated until there are no more objects in LocalObjectSync 264. When there are no objects remaining in LocalObjectSync 264, the object sync process is considered complete 282.

If a content sync is currently in progress 266, then the content sync process is considered complete 282. If it is not, then the system initializes a content sync thread 268. If the number of objects pending in LocalContentSync is greater than zero (0) 270, the system calls the getContent(nextContentGuid) function 272 which results in the server streaming the requested content 274 and the system saving the file into the content directory 276. The system then removes the content entry from LocalContentSync 278. This process is repeated until there is no more content in LocalContentSync 280. When there is no content remaining in LocalContentSync 280, the content sync process is considered complete 282.

FIG. 9: Overall Network Architecture illustrates the general architecture of a system that operates in accordance with one embodiment of the present invention. As shown in FIG. 9, a plurality of graphical user interface (GUI) displays 305, 307, 309 are presented on a plurality of user interface devices 304, 306, 308 connected to a system 300 via the Internet 302. The user interface may be any device capable of presenting data, including, but not limited to, cellular telephones, television sets or hand-held "personal digital assistants." As used herein, the term "Internet" generally refers to any collection of distinct networks working together to appear as a single network to a user. The term refers to the so-called world wide "network of networks" that are connected to each other using the Internet protocol (IP) and other similar protocols. The Internet provides file transfer, remote log in, electronic mail, news and other services. As described herein, the exemplary public network of FIG. 9 is for descriptive purposes only. Although the description may refer to terms commonly used in describing particular public networks such as the Internet, the description and concepts equally apply to other public and private computer networks, including systems having architectures dissimilar to that shown in FIG. 9. For example, and without limitation thereto, the system of the present invention can find application in public as well as private networks, such as a closed university social system, or the private network of a company.

The system 300 is connected to the Internet 102 through a router 301 and a switch 310. As is well known in the relevant art(s), routers forward packets between networks. The router 301 forwards information packets between the system 300 and devices 304, 306, 308 over the Internet 302. The switch 310 may act as a gatekeeper to and from the Internet 302. The components appearing in the system 300 refer to an exemplary combination of those components that would need to be assembled to create the infrastructure in order to provide the tools and services contemplated by the present invention. As will be apparent to one skilled in the relevant art(s), all of the components "inside" of the system 300 may be connected and may communicate via a wide or local area network (WAN or LAN).

The system 300 includes an application server 340 or a plurality of application servers 340, 350. Also included is a mail server 360, which sends and receives electronic messages to and from devices 304, 306, 308. Also included are the database software 322 and a database 324.

The system 300 sends out data in response to requests from users of the system 300. That is, the system 300 provides the GUI 305, 307, 309 to users of the system. This data sent to the user's device 304, 306, 308 would result in GUI screens 305, 307, 309 being displayed.

The system 300 also includes a second switch, not shown, that allows the components of the system to be interconnected in a local area network (LAN) or a wide area network (WAN). Thus, data can be transferred to and from the various components of the system 300.

As will be appreciated by those skilled in the relevant art(s), this configuration of a router 301 and switch 310 is flexible and can be omitted in certain embodiments. Additional routers 314 and/or switches 316 can also be added.

The application server 340 may include a central processing unit (CPU), a random access memory (RAM) for temporary storage of information, and a read only memory (ROM) for permanent storage of information. Application server 340 may be generally controlled and coordinated by operating system software. The operating system controls allocation of system resources and performs tasks such as processing, scheduling, memory management, networking and I/O services, among other things. Thus, the operating system resident in system memory and executed by CPU coordinates the operation of the other elements of the system 300.

Although the description of the application server 340 may refer to terms commonly used in describing particular computer servers, the description and concepts equally apply to other processing systems, including systems having architectures dissimilar to that shown in FIG. 9.

The mail server 360 is a repository for e-mail messages received from the Internet 302. It also manages the transmission of electronic messages ("electronic mail" or "e-mail").

The mail server 360 consists of a storage area, a set of user definable rules, a list of users and a series of communication modules.

The databases 320, 322 store software, descriptive data, digital images, system data and any other data item required by the other components of the system. The databases may be provided, for example, as a database management system (DBMS), and object-oriented database management system (ODBMS), a relational database management system (e.g. DB2, ACCESS etc.), a file system or another conventional database package. Thus, the databases 320, 322 can be implemented using object-oriented technology or via text files. Further, the databases 320, 322 can be accessed via a Structured Query Language (SQL) or other tools known to one of ordinary skill in the art.

Alternative Embodiments

There are various possibilities with regard to the use of the synchronization flow FIG. 8: Synchronization Flow depicts. The synchronization system is designed so that it can serve to deliver content and objects of any type to a plurality of users with or without continuous Internet access. The system is designed to handle both very large content items and very small data items. While a particular implementation of the system involves using the synchronization system to transfer videos, messages, work flow diagrams, tests, and performance statistics, the synchronization system could be used independently with any one or a plurality of those applications or to manage any type of data transfer over networks.

Furthermore, the invention of the team communication platform is applicable to any one or a plurality of numerous team environments where communication and team interaction are important. These environments include, but are not limited to, team sports, healthcare, education, government, and business.

Below is a listing of a variety of embodiments that, while not exhaustive, are illustrative:
1. A portal system for team communication wherein knowledge can be transferred between team leaders and team members digitally.
2. The portal system of embodiment 1 wherein a user logs into said system by entering a valid password or valid biometric data and is then presented with a plurality of program frame items.
3. The portal system of embodiment 2 wherein said program frame items comprise links to a home item.
4. The portal system of embodiment 2 wherein said program frame items comprise links to a messaging item.
5. The portal system of embodiment 2 wherein said program frame items comprise links to a video library item.
6. The portal system of embodiment 2 wherein said program frame items comprise links to a knowledge check item.
7. The portal system of embodiment 2 wherein said program frame items comprise links to a reports item.
8. The portal system of embodiment 2 wherein said program frame items comprise links to a work flow diagrams item.
9. The portal system of embodiment 2 wherein said program frame items comprise links to a performance analyzer item.
10. The portal system of embodiment 2 wherein said program frame items comprises an announcement ticker for displaying announcement feeds.
11. The portal system of embodiment 1 wherein said system comprises a home landing page for the portal that serves as a user's dashboard.
12. The portal system of embodiment 11 wherein said home landing page comprises a messaging preview window that displays a subset of recently received messages.
13. The portal system of embodiment 11 wherein said home landing page comprises a performance dashboard, said performance dashboard comprising means for communicating displays personal and team performance highlights, means for tracking both personal and team goals, or a combination thereof.
14. The portal system of embodiment 11 wherein said home landing page comprises a task summary for the user that lists all of the user's system tasks that have not yet been completed.
15. The portal system of embodiment 14 wherein said task summary comprises pending exams in the knowledge check component.
16. The portal system of embodiment 14 wherein said task summary comprises unviewed work flows.
17. The portal system of embodiment 14 wherein said task summary comprises unviewed videos.
18. The portal system of embodiment 14 wherein said task summary comprises unviewed reports.
19. The portal system of embodiment 1 wherein said system comprises a messaging component for intra-team communication.
20. The portal system of embodiment 19 wherein said messaging component comprises a reply to message functionality that allows the user to reply to any message containing text and/or drawing or ink with a reply containing either basic text entered with a keyboard and/or drawing or ink entered with an input device such as a stylus or a mouse, and rich content attached to the message.
21. The portal system of embodiment 19 wherein said messaging component includes the ability to star, or mark, a message.
22. The portal system of embodiment 21 wherein said messaging component comprises a create message functionality that allows the user to create a new message by entering basic text with a keyboard and/or drawing or ink from an input device such as a stylus or a mouse, attach rich content to the message.
23. The portal system of embodiment 22 wherein said rich content comprises links to work flow diagrams.
24. The portal system of embodiment 22 wherein said rich content comprises links to videos.
25. The portal system of embodiment 22 wherein said rich content comprises links to reports.
26. The portal system of embodiment 1 wherein said system comprises a video component for viewing and annotating videos.
27. The portal system of embodiment 26 wherein said video component comprises the ability to record annotated playback sequences and select users to send said annotated playback sequences.
28. The portal system of embodiment 27 wherein said annotated playback sequences comprises the ability to record a sequence of playback modes including various playback speeds, playback directions, pause points and durations for each mode.
29. The portal system of embodiment 27 wherein said annotated playback sequences comprises the ability to record drawn or ink annotations, and audio recordings integrated with a playback sequence.

30. The portal system of embodiment 27 wherein a summary view of each said annotated playback sequence is listed on the screen in a format that allows the user to readily access the full annotated playback sequence.

31. The portal system of embodiment 27 wherein said video component comprises the ability to view annotated playback sequences including the recorded playback modes along with the drawn or ink annotations and audio recordings.

32. The portal system of embodiment 26 wherein said video component comprises the ability to star, or mark, a video.

33. The portal system of embodiment 26 wherein said video component comprises functionality for the user to annotate video and select users to send said annotations.

34. The portal system of embodiment 33 wherein said annotations comprises drawn or ink annotations from an input device on the video linked to a section or frame of video.

35. The portal system of embodiment 33 wherein said annotations comprises text annotations on the video linked to a section or frame of video.

36. The portal system of embodiment 33 wherein said annotations comprise audio recordings linked to a section or frame of video.

37. The portal system of embodiment 33 wherein a summary view of each said annotation is listed on the screen in a format that allows the user to readily access the full annotation.

38. The portal system of embodiment 33 wherein a video timeline displaying a user's progress through the video is displayed.

39. The portal system of embodiment 33 wherein said annotations result in the video player pausing when it reaches the section of video or frame of video containing said annotation, at which point said annotation is presented to the user.

40. The portal system of embodiment 33 wherein the creation of said annotations results in the addition or an indicator on the video timeline, signifying the section or frame of video associated with the annotation.

41. The portal system of embodiment 40 wherein the user can drag the seek bar to the proximity of the indicator and the seek bar automatically snaps to the indicator's location.

42. The portal system of embodiment 1 wherein said system comprises a knowledge check component for testing.

43. The portal system of embodiment 42 said knowledge check component comprises functionality for the user to create or take tests and functionality for grading the tests.

44. The portal system of embodiment 43 wherein said knowledge check component can automatically send test grades and responses to team leaders for review.

45. The portal system of embodiment 43 wherein said questions comprises video questions that could require the user to select an object on the video or answer questions based off the video, such as drawing a certain shape or pattern or answering multiple choice or fill-in-the blank questions.

46. The portal system of embodiment 45 wherein said video questions allow the user to specify the point in the video at which to begin playback and the point in the video at which to end playback when answering the question.

47. The portal system of embodiment 45 wherein said video questions can be automatically graded by comparing the pattern the user has drawn to the pattern of the correct answer drawn by the creator of the test.

48. The portal system of embodiment 43 wherein said questions comprises work flow or answer questions based off the work flow diagram, such as selecting or highlighting a section of the work flow diagram.

49. The portal system of embodiment 48 wherein said work flow diagram questions can be automatically graded by comparing the pattern the user has drawn to components of the workflow or a pattern drawn as the correct answer by the test creator.

50. The portal system of embodiment 1 wherein said system comprises a reports component.

51. The portal system of embodiment 50 wherein said report component comprises the ability to star, or mark, a report or a section of a report.

52. The portal system of embodiment 50 wherein said report component comprises functionality for the user to view reports with integrated content.

53. The portal system of embodiment 52 wherein said integrated content comprises links to work flow diagrams.

54. The portal system of embodiment 52 wherein said integrated content comprises links to videos.

55. The portal system of embodiment 1 wherein said system comprises a work flow diagrams component.

56. The portal system of embodiment 55 wherein said report component comprises the ability to star, or mark, a report or a section of a report.

57. The portal system of embodiment 55 wherein said work flow diagrams component comprises functionality for the user to view work flow diagrams with integrated content.

58. The portal system of embodiment 57 wherein said integrated content comprises links to reports.

59. The portal system of embodiment 57 wherein said integrated content comprises links to videos.

60. The portal system of embodiment 57 wherein said integrated content comprises links to knowledge check components for self testing.

61. The portal system of embodiment 1 wherein said system is implemented for sports teams with practice and game videos, playbooks and scouting reports.

62. The portal system of embodiment 1 wherein said system is implemented for a healthcare organization.

63. The portal system of embodiment 1 wherein said system is implemented for an educational organization.

64. The portal system of embodiment 1 wherein said system is implemented for a governmental organization.

65. The portal system of embodiment 1 wherein said system is implemented for a business.

66. A synchronization system wherein objects and content can be sent between a central server and a plurality of client systems over a network connection.

67. The synchronization system of embodiment 66 wherein said network connection is an Internet connection.

68. The synchronization system of embodiment 66 wherein said network connection is an Intranet connection.

69. The synchronization system of embodiment 66 wherein said network connection is wireless connection.

70. The synchronization system of embodiment 66 wherein the synchronization process is facilitated through a send action process and a retrieval process.
71. The synchronization system of embodiment 66 wherein the synchronization process is initiated by a sync timer or manually by the user.
72. The synchronization system of embodiment 71 wherein said system confirms a network connection and prompts the user if the synchronization was manually initiated.
73. The synchronization system of embodiment 72 wherein said system checks to see if a synchronization process has already been initialized before proceeding by storing the current time in a temporary format and creating a lists by querying for objects and content created or modified since the last synchronization.
74. The synchronization system of embodiment 73 wherein said system performs clean up functions on said lists by filtering out objects and content already in the synchronization table and filtering out content already on the local machine before appending all remaining list items to the synchronization table and logging the temporary time recorded early.
75. The synchronization system of embodiment 74 wherein said list items and synchronization table contents are stored as globally unique identifiers.
76. The synchronization system of embodiment 74 wherein said system checks to see if it is currently sending objects or content before retrieving pending send actions from the local table and, as long as the number of said send actions is greater than zero, said system calls the appropriate send action web service that results in a central server processes action that updates the database and makes a duplex call back to the client that results in the item being removed from the local table until the number of said send actions is zero at which point the system begins the retrieval stage.
77. The synchronization system of embodiment 74 wherein said system handles object and content synchronization as separate and distinct threads.
78. The synchronization system of embodiment 77 wherein said object synchronization is initialized by said system if an object synchronization is not already in progress and, if one is not, said object synchronization process calls a get object function that results in the server sending the object and the system setting a received date as long as the number of object pending in the local object synchronization table is greater than zero.
79. The synchronization system of embodiment 78 wherein said content synchronization is initialized by said system if an content synchronization is not already in progress and, if one is not, said content synchronization process calls a get content function that results in the server streaming the content and the system saving the file in the content directory and removing the content entry from the local content synchronization table.
80. The portal system of embodiment 1 wherein the system comprises a presentations component for creating, viewing, and sharing with other users presentations consisting of sequences of slides containing videos, work flow diagrams, text, and images.
81. The portal system of embodiment 80 wherein a video on a presentation slide can contain drawn or ink annotations, text annotations, and audio recordings.
D. The portal system of embodiment 80 wherein said video on a presentation slide allows the user to specify the point in the video at which to begin playback and the point in the video at which to end playback when viewing the slide.

From the descriptions above, a number of advantages of the invention become evident:

(a) Any time a team member has a question or comment for a team leader or another team member, that individual can directly link a work flow diagram or video into his or her message and receive feedback immediately.

(b) The invention takes a team's existing video editing infrastructure, work flow diagramming, reporting processes, presentations, and tests and shifts these activities to an interactive, easy-to-use, digital platform, providing the team with a more powerful and secure means of communication, training, and team management.

(c) The invention provides team leaders and team members the opportunity to deliver personalized comments integrated into a video to any other team member or leader. Comments can include sketches directly on the video, typed notes, handwritten notes, and voice recordings at multiple points throughout a video clip. Videos can be integrated into any other area of the invention, including the work flow diagrams, reports, knowledge check, and messages. Team leaders and team members can review any clip in their personalized video library at any time with full annotations automatically displayed during playback.

(d) The invention provides team leaders and team members the opportunity to navigate through the most updated diagrams of work flows and strategies that can have videos, voice recordings, written comments, and report information directly linked to them. Furthermore, these diagrams can be updated and transferred to every team member's computer when synced and can be stored with multiple variations based on various scenarios. Team members can quickly "self-test" themselves on any work flow diagram by wiping instruction sets off the diagram, recreating them, and receiving immediate feedback from the system.

(e) The invention provides team leaders the opportunity to easily create customized tests for any team member or group of team members, with test questions that require an individual to react to scenarios through videos, confirm understanding of work flows through work flow diagrams, and/or answer traditional multiple choice questions. Team members receive immediate feedback on the accuracy of their answers and team leaders receive continuous updates on a player's performance on tests.

(f) Presentations. Team members can create presentations in the system that directly integrate video, annotations, work flow diagrams, reports, text, and images into a sequence of slides that can be viewed and shared within the portal.

(g) The invention provides an interface for team leaders and team members to drill down to various levels of information, allowing for more detailed data than paper reports can provide. The interface facilitates the linking of videos directly into these reports, adding an interactive element that brings the reports to life for team members. Report information can also be incorporated in other relevant areas of the system, with past reports maintained in the system so they can be easily accessed at a later date.

(h) The invention allows team leaders to track a team member's usage of the system, including time spent actively reviewing each work diagram and studying video, as well as performance on tests and allows team leaders to review the most up-to-date team reports with the ability to review historical reports on all team members.

Accordingly, the reader will see that this invention revolutionizes team communications by taking what are currently unstructured, informal lines of communication and formalizing them in a way that maximizes the potential knowledge transfer. This invention places technology directly in the hands of team leaders and team members, providing a comprehensive solution that takes a holistic approach at addressing the challenges involved in team communication. This invention provides a team with a mobile, easy-to-use solution that allows for the creation and transfer of personalized content within teams, reducing the duplication of work.

Although the description above contains much specificity, it should not be construed as limiting the scope of the invention but as merely providing illustrations of some of the presently preferred embodiments of this invention. For example, the synchronization system has been designed so that it can serve to deliver both very large content items and very small data items of any type to a plurality of users with or without continuous Internet access. While a particular implementation of the system involves using the synchronization system to transfer videos, messages, work flow diagrams, tests, and performance statistics, the synchronization system could be used independently with any one or a plurality of those applications or to manage any type of data transfer over networks. Furthermore, the invention of the team communication platform can be applied to any one or a plurality of numerous team environments where communication and team interaction are important. These environments include, but are not limited to, team sports, healthcare, education, government, and business.

Thus, the scope of the claim should be determined by the appended claims and their legal equivalents, rather than by the examples given.

What is claimed is:

1. A portal system for team communication relating to at least one sporting play of a sports team, the portal system comprising:
    a processor operable to execute one or more components, the processor configured to communicatively couple to a display for controlling content of the display;
    a home component for causing the processor to display a home item at the display, the home item including a task summary having at least one task remaining relating to the at least one sporting play;
    a messaging component for causing the processor to display a messaging frame;
    a video component for causing the processor to display a video library item, the video library item including at least one selectable video relating to the at least one sporting play, the at least one selectable video including a video frame having a video annotation corresponding to the at least one sporting play, the video component configured to cause the processor to automatically display the video annotation during playback of the at least one selectable video, the video annotation comprising a personalized comment;
    a work flow diagram component for causing the processor to display a work flow diagram item relating to the at least one sporting play, the work flow diagram item comprising at least one selectable work flow diagram, the work flow diagram component configured to cause an update of a modified work flow diagram item at a remote computing device upon detection of a synchronization event of the remote computing device; and
    a reporting component for causing the processor to display a report item, the report item including at least one selectable report associated with the sports team, the reporting component including a report viewer configured to cause the processor to display a report selected from the at least one selectable report, the selected report including integrated content having one or more embedded links to a work flow diagram viewer of the work flow diagram component associated with the selected report and to a video viewer of the video component associated with the selected report;
    a knowledge check component for causing the processor to display a customizable knowledge check item, the customizable knowledge check item including at least one selectable test relating to the at least one sporting play, the customizable knowledge check component is configured to cause the processor to present a scenario relating to the at least one sporting play and configured to receive an input corresponding to a reaction within the context of the scenario, the customizable knowledge check component configured to furnish immediate feedback regarding an accuracy of the input pertaining to the context of the scenario,
    wherein the selected report provides access to at least one of the work flow diagram viewer or the video viewer via the one or more embedded links, the work flow diagram viewer configured to cause display of the at least one selectable work flow diagram and the video viewer configured to cause display of the at least one selectable video.

2. The portal system as recited in claim 1, wherein the at least one selectable test comprises a video question, wherein the knowledge check component is configured to cause the processor to receive a selection proximate to an object within the video question corresponding to a reaction within the context of the scenario.

3. The portal system as recited in claim 1, wherein the at least one selectable test comprises a modifiable work flow diagram question associated with a work flow diagram content, the modifiable work flow diagram question having a modifiable work flow diagrams based upon the work flow diagram content and at least one question based upon the work flow diagram content.

4. The portal system as recited in claim 1, wherein the work flow diagram component further includes a work flow diagram viewer for causing the processor to display a selected work flow diagram selected from the at least one selectable work flow diagram, the selected work flow diagram including integrated content having embedded links to a report viewer of the reporting component associated with the selected work flow diagram, to a video viewer of the video component associated with the selected work flow diagram, and to a self tester of the knowledge check component associated with the selected work flow diagram.

5. The portal system as recited in claim 4, wherein the video viewer is configured to cause the processor to display at least one selectable video associated with the selected work flow diagram.

6. The portal system as recited in claim 1, wherein the video viewer is configured to cause the processor to display at least one video included in the video library item, the at least one video associated with the report.

7. The portal system as recited in claim 1, wherein the personalized comment comprises at least one of a sketch, a typed note, a handwritten note, or a voice recording.

8. The portal system as recited in claim 1, wherein the work flow diagram is a user-recreated sporting play diagram having a user-selected instruction set.

9. The portal system as recited in claim 4, wherein the home component includes a performance dashboard, the performance dashboard configured to cause the processor to display at least one of a personal performance highlight or a team performance highlight and to display at least one of a personal goal relating to the sports team or a team goal relating to the sports team.

10. The portal system as recited in claim 1, wherein the messaging component is configured to cause the processor to transmit a second selectable video to a user-specified recipient, the second selectable video including a video frame having a user-specified video annotation.

11. The portal system as recited in claim 10, wherein the user-specified video annotation comprises at least one of a user-defined sketch or a user-defined typed note.

12. The portal system as recited in claim 1, wherein the reporting component is further configured to cause the processor to display a user work flow diagram review time of the at least one selectable work flow diagram, a user video review time of the at least one selectable video, and a user performance score associated with a test.

13. A portal system for team communication between various members of a sports team, the portal system comprising:
a processor operable to execute one or more components, the processor configured to communicatively couple to a display for controlling content of the display;
a home component for causing the processor to display a home page at the display, the home page including a task summary having at least one task remaining relating to a context of at least one sporting play;
a messaging component for causing the processor to display a messaging frame relating to the context of the at least one sporting play;
a sporting play component for causing the processor to display a sporting play diagram item, the sporting play diagram item comprising at least one selectable sporting play diagram relating to the context of the at least one sporting play;
a sporting play video component for causing the processor to display a sporting play video library item, the sporting play video library item including at least one selectable sporting play video, the at least one selectable sporting play video including a sporting play video frame relating to the context of the at least one sporting play, wherein the sporting video frame further includes a pre-generated video annotation relating to the context of the at least one sporting play, the sporting play video component configured to cause the processor to automatically display the pre-generated video annotation during playback of the at least one selectable video, the pre-generated video annotation comprising at least one of a sketch, a typed note, a handwritten note, or a voice recording;
a knowledge check component for causing the processor to display a knowledge check item, the knowledge check item comprising at least one selectable sporting play test relating to the context of the at least one sporting play, the knowledge check component configured to cause the processor to determine an accuracy of a user-created sporting play diagram with reference to a selected sporting play diagram of the at least one selectable sporting play diagram; and
a reporting component for causing the processor to display a report item, the report item including at least one selectable report relating to the context of the at least one sporting play, the reporting component including a report viewer configured to cause the processor to display a report selected from the at least one selectable report, the selected report including integrated content having one or more embedded links to at least one of a video viewer of the sporting play video component associated with the report or a sporting play viewer of the sporting play component associated with the report,
wherein the selected report provides access to at least one of the sporting play viewer or the video viewer via the one or more embedded links, the sporting play viewer configured to cause display of the at least one selectable sporting play diagram and the video viewer configured to cause display of the at least one selectable video.

14. The portal system as recited in claim 13, wherein the reporting component further includes a report viewer for causing processor to display a selected report selected from the at least one selectable report, the selected report including integrated content having embedded links to a sporting play diagram viewer of the sporting play diagram component and to a sporting play video viewer of the sporting play video component.

15. The portal system as recited in claim 13, wherein the home component includes a performance dashboard, the performance dashboard for causing the processor to display at least one of a personal sporting performance highlight or a team sporting performance highlight and to display at least one of a personal sporting goal a team sporting goal.

16. The portal system as recited in claim 13, wherein the messaging component is further configured to cause the processor to transmit a second selectable sporting play video to a user-specified recipient, the second selectable sporting play video including a video frame having a user-specified video annotation.

17. The portal system as recited in claim 16, wherein the user-specified video annotation comprises at least one of a user-defined sketch or a user-defined typed note.

18. The portal system as recited in claim 13, wherein the reporting component is further configured to cause the processor to display a sporting play diagram review time of the at least one selectable sporting play diagram, a user sporting play video review time of the at least one selectable sporting play video, and a user performance score of a test relating to the context of the at least one sporting play.

19. The portal system as recited in claim 13, wherein the at least one selectable sporting play test includes at least one of: a new selectable sporting play test relating to the context of the at least one sporting play, an in-progress selectable sporting play test relating to the context of the at least one sporting play, or a completed selectable sporting play test relating to the context of the at least one sporting play.

20. A portal system for team communication relating to at least one sporting play, the portal system comprising:
a processor operable to execute one or more components, the processor configured to communicatively couple to a display for controlling content of the display;
a home component for causing the processor to display a home page at the display, the home page including a task summary having at least one task remaining relating to a context of the at least one sporting play;
a messaging component for causing the processor to display a messaging frame, the messaging frame including at least one message relating to the context of the at least one sporting play;
a sporting play component for causing the processor to display a sporting play diagram item, the sporting play diagram item comprising at least one selectable sporting play diagram relating to the context of the at least one sporting play, the sporting play component configured to cause an update of a modified sporting play diagram item at a remote computing device upon detection of a synchronization event of the remote computing device;

a sporting play video component for causing the processor to display a sporting play video library item, the sporting play video library item including at least one selectable sporting play video, the at least one selectable sporting play video including a sporting play video frame having a user-specified video annotation and a user-specified audio annotation, the sporting play video frame relating to the context of the at least one sporting play, the user-specified video annotation and the user-specified audio annotation relating to the context of the at least one sporting play, the sporting play video component configured to cause the processor to automatically display the user-specified video annotation and the user-specified audio annotation during playback of the at least one selectable sporting play video, the user-specified video annotation comprising at least one of a sketch, a typed note, a handwritten note, or a voice recording;

a knowledge check component for causing the processor to display a knowledge check item, the knowledge check item comprising at least one selectable video sporting play test relating to the context of the at least one sporting play, the knowledge check component is configured to cause the processor to present a scenario relating to the at least one sporting play and configured to receive an input corresponding to a reaction within the context of the scenario and to furnish immediate feedback regarding an accuracy of the input to the context of the scenario; and a reporting component for causing the processor to display a report item, the report item including at least one selectable report relating to the context of the at least one sporting play, the reporting component including a report viewer configured to cause the processor to display a scouting report selected from the at least one selectable report, the scouting report including integrated content having one or more embedded links to at least one of a video viewer of the sporting play video component associated with the report or a sporting play viewer of the sporting play component associated with the report, wherein the selected report provides access to at least one of the sporting play viewer or the video viewer via the one or more embedded links, the sporting play viewer configured to cause display of the at least one selectable sporting play diagram and the video viewer configured to cause display of the at least one selectable video.

* * * * *